(12) United States Patent
Algawi et al.

(10) Patent No.: US 12,016,795 B2
(45) Date of Patent: Jun. 25, 2024

(54) CLUTCH FOR DISPOSABLE PUMP CARTRIDGE

(71) Applicant: JOHNSON & JOHNSON SURGICAL VISION, INC., Irvine, CA (US)

(72) Inventors: Yehuda Algawi, Binyamina (IL); Assaf Govari, Haifa (IL); Eran Aharon, Haifa (IL); Ilya Sitnitsky, Nahariya (IL); Stanislav Katzir, Hadera (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 343 days.

(21) Appl. No.: 17/318,682

(22) Filed: May 12, 2021

(65) Prior Publication Data

US 2022/0362056 A1 Nov. 17, 2022

(51) Int. Cl.
| | |
|---|---|
| *F16D 41/067* | (2006.01) |
| *A61F 9/007* | (2006.01) |
| *A61M 1/00* | (2006.01) |
| *F16D 15/00* | (2006.01) |

(52) U.S. Cl.
CPC .......... *A61F 9/00745* (2013.01); *A61M 1/60* (2021.05); *F16D 15/00* (2013.01); *F16D 41/067* (2013.01); *A61M 2210/0612* (2013.01)

(58) Field of Classification Search
CPC ........... F16D 15/00; F16D 41/064–067; F16D 43/211
USPC .......................................................... 192/38
See application file for complete search history.

(56) References Cited

U.S. PATENT DOCUMENTS

| | | | |
|---|---|---|---|
| 2,815,838 A | 12/1957 | Dodge | |
| 3,174,598 A | * 3/1965 | Mattson | ................... F02N 15/06 192/45.01 |
| 4,714,803 A | * 12/1987 | Lederman | ............. F16D 41/067 192/113.34 |
| 5,421,780 A | 6/1995 | Vukovic | |
| 5,501,580 A | 3/1996 | Barrus et al. | |

(Continued)

FOREIGN PATENT DOCUMENTS

| | | |
|---|---|---|
| CN | 111609054 A * | 9/2020 |
| DE | 312191 C | 12/1917 |

(Continued)

*Primary Examiner* — Stacey A Fluhart
(74) *Attorney, Agent, or Firm* — Johnson & Johnson Surgical Vision, Inc.

(57) ABSTRACT

An apparatus for mechanically coupling a motor to a rotor includes an outer ring including an inner surface shaped to define multiple recesses, an inner ring disposed within the outer ring and shaped to define multiple compartments having respective outer openings, which face the outer ring, and respective inner openings opposite the outer openings, and multiple gripping elements disposed within the compartments, respectively. The inner ring is configured to receive the rotor while the compartments are aligned with the of recesses, by virtue of the gripping elements sitting at least partially within the recesses. The outer ring is configured to couple with a shaft coupled with the motor such that rotation of the shaft by the motor causes the compartments to become misaligned with the recesses, thereby causing the outer ring to push the gripping elements, through the outer openings, against the rotor, through the inner openings.

5 Claims, 10 Drawing Sheets

(56) References Cited

U.S. PATENT DOCUMENTS

| | | | |
|---|---|---|---|
| 6,000,512 A * | 12/1999 | Cronin | F16D 41/067 |
| | | | 192/38 |
| 6,006,881 A * | 12/1999 | Lederman | F16D 41/067 |
| | | | 192/113.32 |
| 7,070,578 B2 | 7/2006 | Leukanech et al. | |
| 7,779,987 B2 * | 8/2010 | Swinderman | B65G 45/12 |
| | | | 73/863.52 |
| 7,827,570 B2 | 11/2010 | Suzuki | |
| 8,986,252 B2 | 3/2015 | Cummings et al. | |
| 9,603,990 B2 | 3/2017 | Woolford | |
| 2001/0011623 A1 * | 8/2001 | Ogata | F16D 41/066 |
| | | | 192/113.32 |
| 2001/0055528 A1 | 12/2001 | Mills | |
| 2005/0049621 A1 | 3/2005 | Feingold et al. | |
| 2006/0083637 A1 | 4/2006 | Marielle | |
| 2010/0297193 A1 | 11/2010 | Archambeau et al. | |
| 2011/0137231 A1 | 6/2011 | Sorensen et al. | |
| 2013/0048384 A1 | 2/2013 | Jarvis et al. | |
| 2013/0092493 A1 | 4/2013 | Hsueh | |
| 2019/0247050 A1 | 8/2019 | Goldsmith | |
| 2022/0186792 A1 * | 6/2022 | Robert | F16D 41/067 |

FOREIGN PATENT DOCUMENTS

| | | | | |
|---|---|---|---|---|
| DE | 9312700 U1 | 11/1993 | | |
| DE | 102016124241 A1 * | 6/2018 | | F16D 41/064 |
| WO | 2020160434 A1 | 8/2020 | | |
| WO | 2021001742 A1 | 1/2021 | | |

\* cited by examiner

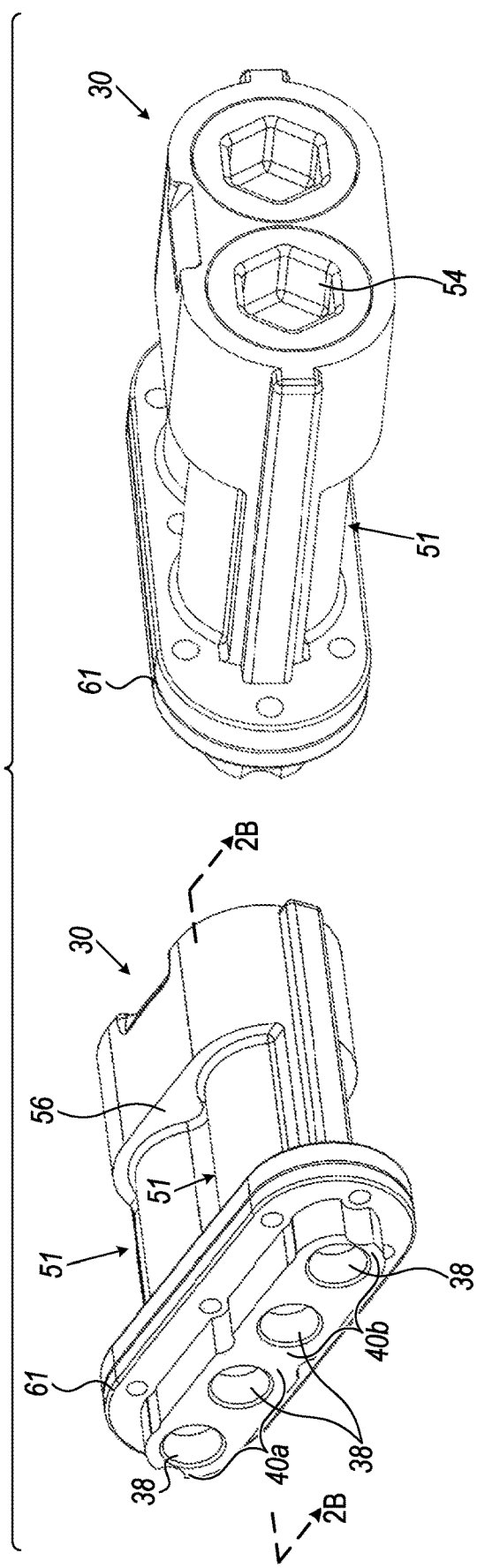
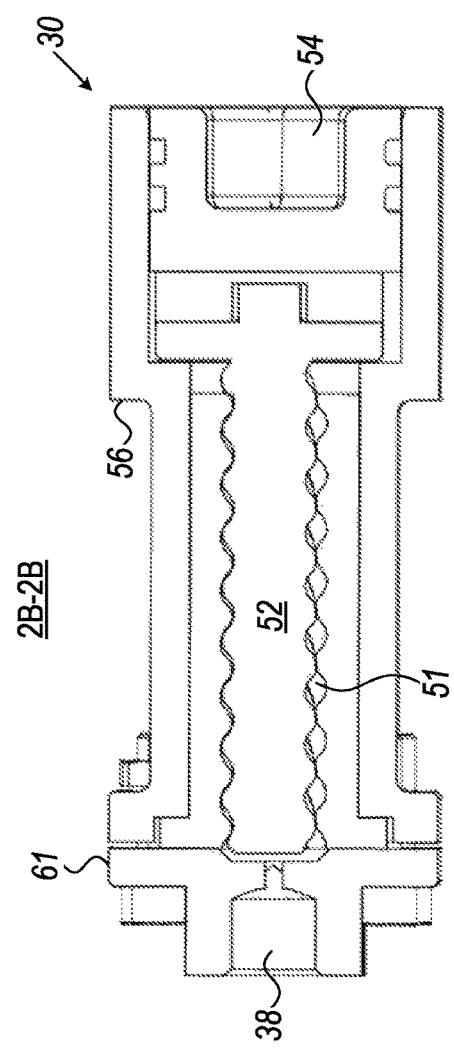
FIG. 2A
FIG. 2B

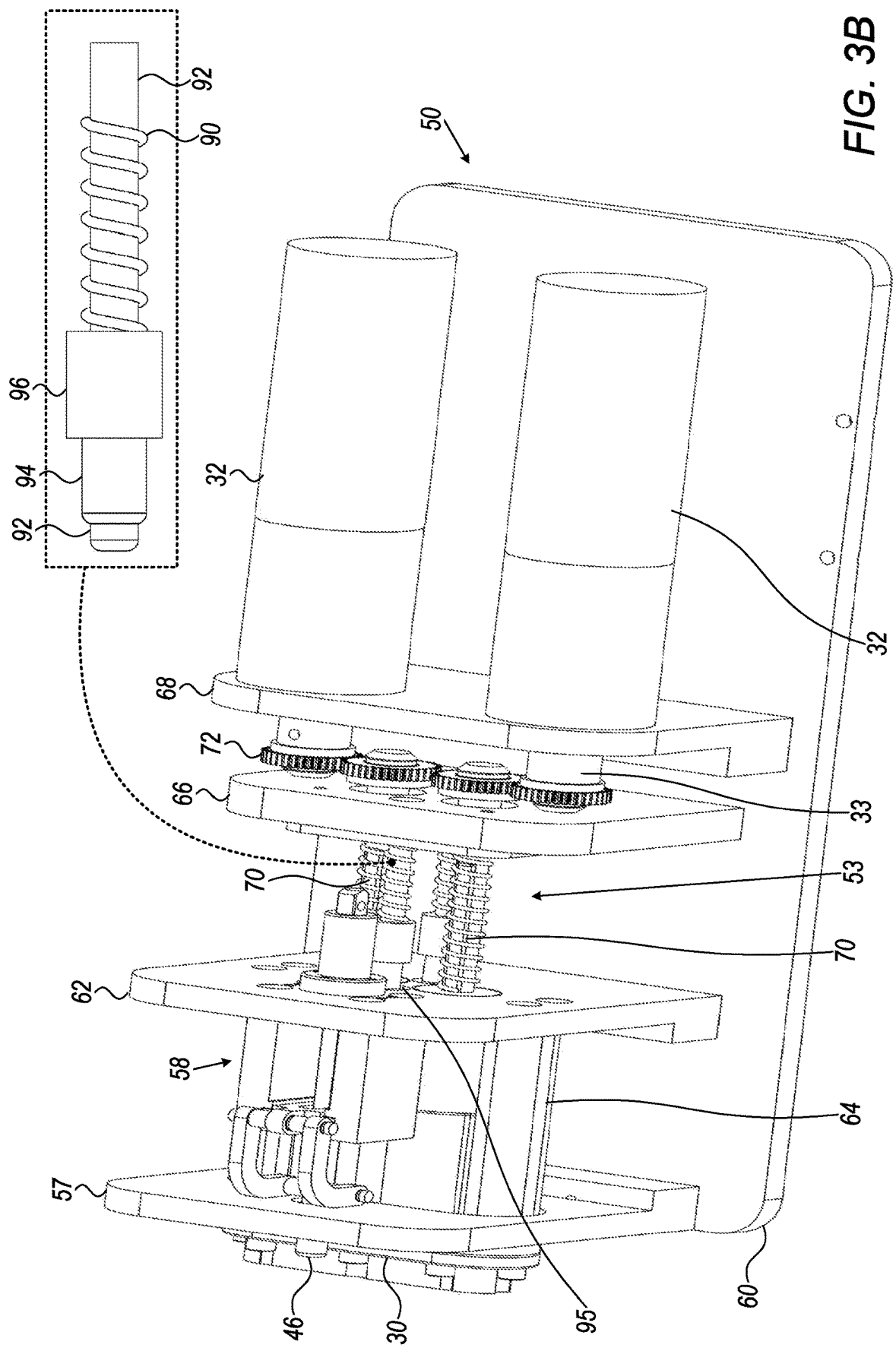

CLUTCH FOR DISPOSABLE PUMP CARTRIDGE

CROSS-REFERENCE TO RELATED APPLICATIONS

The present application is related to (i) an application entitled "Disposable pump cartridge", U.S. application Ser. No. 17/318,665, filed May 12, 2021, currently pending, and (ii) an application entitled "Locking mechanism for disposable pump cartridge", U.S. application Ser. No. 17/318,710, filed May 12, 2021, currently pending.

FIELD OF THE INVENTION

The present invention is related generally to the field of eye surgery, and particularly to phacoemulsification procedures.

BACKGROUND

International Patent Application 2021/001742 describes a surgical handpiece including a proximal segment and a distal segment. The distal segment may include an emulsifying tip, an irrigation output in fluidic communication with the irrigation input and capable of supplying irrigating fluid to a surgical site, and a progressing cavity pump aspirator in fluidic communication with an aspiration port and capable of aspirating the emulsified material to a material collection point through an aspiration connection. The pump may include a stator and a rotor rotationally associated with the stator to effectuate pumping, via the stator cavities, of the emulsified material from the aspiration port in the distal segment through the proximal section.

SUMMARY OF THE INVENTION

There is provided, in accordance with some embodiments of the present invention, an apparatus including a base, including two motors and a mechanical coupling mechanism. The apparatus further includes a cartridge, shaped to define two stators and respective pairs of ports in fluidic communication with the stators. The cartridge is removably insertable into the base and includes two rotors disposed, respectively, within the stators. The mechanical coupling mechanism is configured to mechanically couple the rotors to the motors, respectively, such that, following insertion of the cartridge into the base, the motors rotate the rotors, thereby pumping fluid through the pairs of ports.

In some embodiments, the base is shaped to define a slot, and the cartridge is removably insertable into the base by virtue of being reversibly slidable through the slot.

In some embodiments, the base further includes:
a lock, configured to lock the cartridge in place upon the insertion of the cartridge; and
a button, configured to release the lock upon a pushing of the button.

In some embodiments,
the cartridge is shaped to define an aperture,
the lock includes a locking element shaped to fit into the aperture, and
the button is configured to release the lock by pushing the locking element from the aperture.

In some embodiments, the lock further includes a spring configured to lock the cartridge in place by holding the locking element in the aperture.

In some embodiments,
the rotors include respective first connectors, each of which has a non-circular shape, and
the mechanical coupling mechanism includes:
two non-circular shafts coupled with the motors, respectively, such that the shafts are rotatable by the motors;
two second connectors, each of which has the non-circular shape, slidably disposed over the shafts, respectively, such that the second connectors are rotatable with the shafts; and
two springs slidably disposed over the shafts, respectively, the springs being configured to couple the shafts with the rotors by pushing the second connectors toward the first connectors such that, upon the second connectors rotating into alignment with the first connectors, the second connectors mate with the first connectors.

In some embodiments, the non-circular shape is a hexagonal shape.

In some embodiments, the first connectors are female and the second connectors are male.

There is further provided, in accordance with some embodiments of the present invention, a method including inserting a cartridge into a base including two motors, the cartridge being shaped to define two stators and respective pairs of ports in fluidic communication with the stators, and including two rotors disposed, respectively, within the stators. The method further includes activating the motors to rotate the rotors, respectively, thereby pumping fluid through the pairs of ports. The method further includes removing the cartridge from the base.

In some embodiments, the method further includes, subsequently to removing the cartridge from the base, disposing of the cartridge.

In some embodiments, activating the motors includes:
causing a first one of the motors to pump the fluid from a reservoir to a distal end of a probe through a first one of the pairs of ports; and
causing a second one of the motors to pump the fluid, together with debris, from the distal end of the probe to a collection container through a second one of the pairs of ports.

In some embodiments, the fluid includes a balanced salt solution.

In some embodiments,
activating the motors includes causing the motors to rotate the rotors while the probe is used to perform a phacoemulsification of a lens of an eye, and
the debris includes pieces of the lens.

There is further in accordance with some embodiments of the present invention, an apparatus for use with a cartridge having an outer surface shaped to define a ridge. The apparatus includes a rigid piece of material configured to lock the cartridge in place by resting against the ridge. The apparatus further includes a button, configured to move the rigid piece of material from the cartridge, thereby unlocking the cartridge, upon a pushing of the button. The apparatus further includes one or more motors and a mechanical coupling mechanism, configured to mechanically couple the motors to the cartridge while the cartridge is locked in place.

In some embodiments, the apparatus further includes at least one spring, configured to:
remain compressed against the cartridge while the cartridge is locked in place, and
decompress following the unlocking of the cartridge, thereby pushing the cartridge.

In some embodiments, the apparatus further includes:

a panel; and at least one rod coupled with the panel, wherein the spring is coiled around the rod with a back end of the spring coupled with the panel, and wherein a front end of the spring is configured to push the cartridge.

In some embodiments, the cartridge is shaped to define one or more stators and includes one or more rotors disposed, respectively, within the stators, and the mechanical coupling mechanism is configured to mechanically couple the motors to the rotors, respectively.

In some embodiments, the outer surface is a top surface of the cartridge, and the rigid piece of material is configured to lock the cartridge in place by hanging over the cartridge such that a bottom of the rigid piece of material rests against the ridge.

In some embodiments, the apparatus further includes a hinge coupled with the button and with the rigid piece of material, and the button is configured to move the rigid piece of material by rotating the hinge.

In some embodiments, the hinge includes:

a first pin, which is coupled with the button;

a second pin, which is coupled with the rigid piece of material; and two swiveling elements, each of which includes one end rotatably coupled with the first pin and a second end rotatably coupled with the second pin, and the button is configured to move the rigid piece of material by swiveling the swiveling elements.

In some embodiments, the button is configured to move along a first axis, a position of the rigid piece of material along the first axis is fixed, and the button is configured to rotate the hinge, thereby moving the rigid piece of material along a second axis perpendicular to the first axis, by virtue of the position of the rigid piece of material along the first axis being fixed.

In some embodiments, the apparatus further includes:

a panel having a location along the first axis that is fixed; and at least one anchoring element coupled with the panel and shaped to define a groove parallel to the second axis, the position of the rigid piece of material along the first axis being fixed by virtue of the rigid piece of material being slidably disposed within the groove.

There is further provided, in accordance with some embodiments of the present invention, a method including inserting a cartridge into a base including a rigid piece of material and one or more motors, thereby causing the rigid piece of material to lock the cartridge in place by resting against a ridge on an outer surface of the cartridge, and causing a mechanical coupling mechanism to mechanically couple the motors to the cartridge. The method further includes unlocking the cartridge by pushing a button so as to move the rigid piece of material from the cartridge.

In some embodiments, the method further includes, subsequently to inserting the cartridge into the base, activating the motors to rotate the rotors, thereby pumping fluid through the stators.

In some embodiments, the fluid includes a balanced salt solution.

There is further provided, in accordance with some embodiments of the present invention, an apparatus for mechanically coupling a motor to a rotor. The apparatus includes an outer ring including an inner surface shaped to define multiple recesses. The apparatus further includes an inner ring disposed within the outer ring and shaped to define multiple compartments having respective outer openings, which face the outer ring, and respective inner openings opposite the outer openings, and multiple gripping elements disposed within the compartments, respectively. The inner ring is configured to receive the rotor while the compartments are aligned with the of recesses, by virtue of the gripping elements sitting at least partially within the recesses. The outer ring is configured to couple with a shaft coupled with the motor such that rotation of the shaft by the motor causes the compartments to become misaligned with the recesses, thereby causing the outer ring to push the gripping elements, through the outer openings, against the rotor, through the inner openings.

In some embodiments, the gripping elements include respective cylindrical pegs.

In some embodiments, the gripping elements include respective balls.

In some embodiments, the outer ring is shaped to define an outer radial aperture, the inner ring is shaped to define an inner radial aperture aligned with the outer radial aperture, and the apparatus further includes a compressible peg passing through the outer radial aperture and the inner radial aperture, the compressible peg being configured to:

become and remain compressed during the rotation of the outer ring, and decompress following the rotation of the shaft, thereby realigning the compartments with the recesses.

In some embodiments, the apparatus further includes a connecting ring coupled with the outer ring behind the inner ring, the outer ring being configured to couple with the shaft by virtue of the connecting ring being fastened to the shaft.

In some embodiments, the apparatus further includes multiple compressible elements arranged around an inner circumference of the inner ring, the compressible elements being configured to compress upon insertion of the rotor into the inner ring, thereby centering the rotor within the inner ring.

There is further provided, in accordance with some embodiments of the present invention, a method including inserting a rotor into an inner ring, which is disposed within an outer ring and is shaped to define multiple compartments having respective outer openings, which face the outer ring, and respective inner openings opposite the outer openings. The outer ring includes an inner surface shaped to define multiple recesses, and is coupled with a shaft coupled with a motor. Multiple gripping elements are disposed within the compartments, respectively, and the compartments are aligned with the recesses, by virtue of the gripping elements sitting at least partially within the recesses. The method further includes activating the motor to rotate the shaft, thereby causing the compartments to become misaligned with the recesses such that the outer ring pushes the gripping elements, through the outer openings, against the rotor, through the inner openings, such that the rotor rotates with the shaft.

In some embodiments, the rotor is disposed within a stator of a cartridge shaped to define a pair of ports in fluidic communication with the stator, and the method further includes pumping fluid through the pair of ports by activating the motor.

In some embodiments, pumping the fluid through the pair of ports includes pumping the fluid, through the pair of ports, from a reservoir to a distal end of a probe.

In some embodiments, the fluid includes a balanced salt solution.

In some embodiments, pumping the fluid through the pair of ports includes pumping the fluid together with debris, through the pair of ports, from a distal end of a probe to a collection container.

In some embodiments, the method further includes performing a phacoemulsification of a lens of an eye during the pumping of the fluid, and the debris includes pieces of the lens.

The present invention will be more fully understood from the following detailed description of embodiments thereof, taken together with the drawings, in which:

BRIEF DESCRIPTION OF THE DRAWINGS

FIG. 2A schematically shows a cartridge from two different perspectives, in accordance with some embodiments of the present invention;

FIG. 2B schematically shows a longitudinal cross section through a cartridge, in accordance with some embodiments of the present invention;

FIGS. 3A-B schematically show a fluidics system from two different perspectives, in accordance with some embodiments of the present invention;

DETAILED DESCRIPTION OF EMBODIMENTS

Overview

Figure 1:
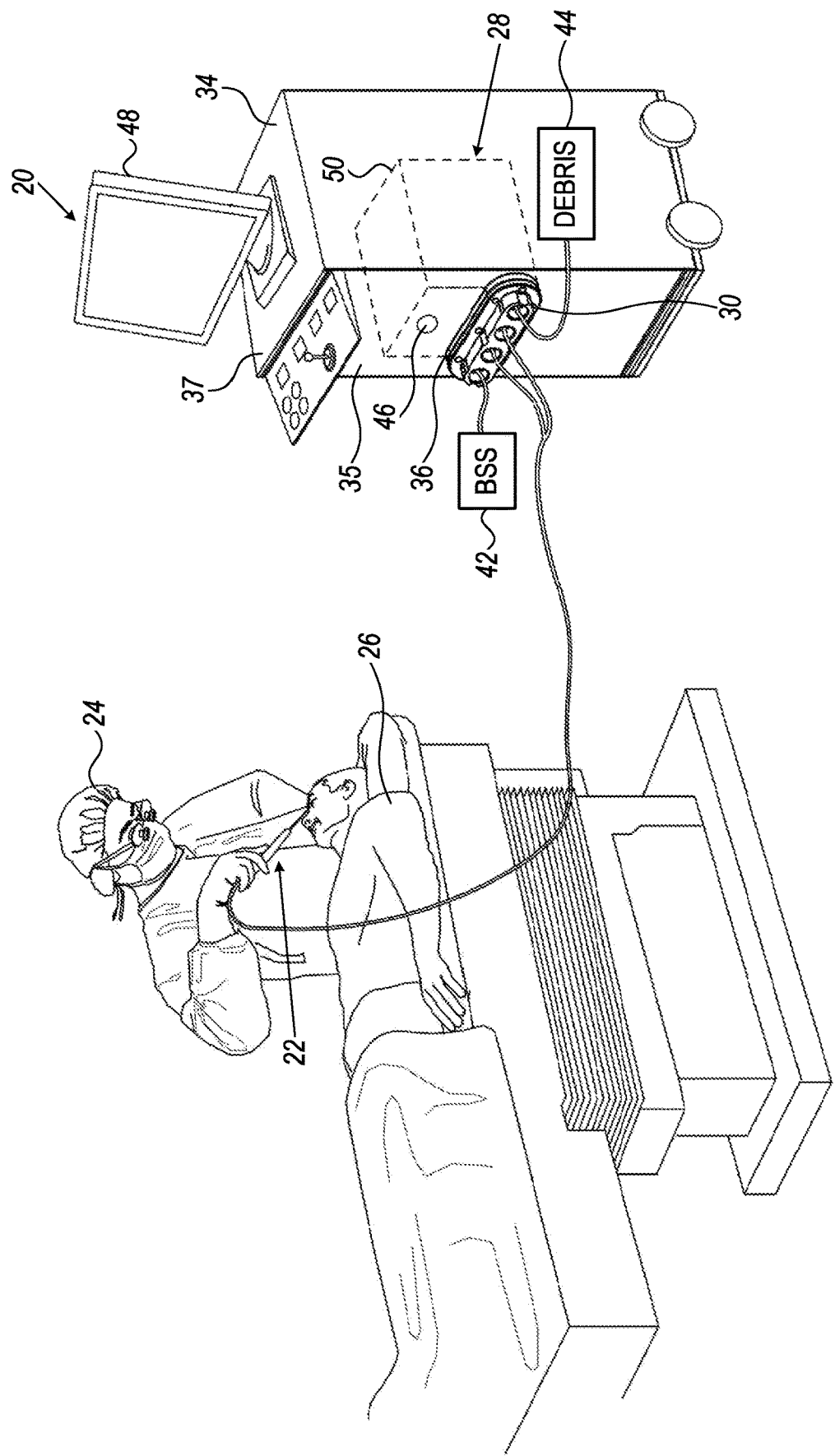
FIG. 1 is a schematic illustration of a phacoemulsification system, in accordance with some embodiments of the present invention.

During a phacoemulsification procedure, fluids are pumped in and out of the eye. One type of pump that may be particularly effective for this purpose is a progressive cavity pump, which comprises a rotor rotatably disposed inside a stator. However, such a pump may be difficult or impossible to sterilize after use, and repeatedly replacing the entire pump apparatus, including any motors, may be prohibitively expensive.

To address this challenge, embodiments of the present invention provide a disposable cartridge comprising two progressive cavity pumps: one pump for pumping fluid to the eye, and another pump for pumping fluid from the eye. The cartridge is inserted into a base, which comprises a pair of motors and a mechanism for mechanically coupling the motors with the pumps. Advantageously, following the phacoemulsification procedure, the relatively inexpensive cartridge may be discarded, while the base may be reused for the next procedure without necessarily requiring any prior cleaning.

Embodiments of the present invention further provide a lock for locking the cartridge following the insertion of the cartridge into the base. In some embodiments, the lock comprises a rigid piece of material that rests against a ridge on the surface of the cartridge, thus inhibiting the cartridge from slipping from the base. In other embodiments, the lock comprises a locking element configured to fit into an aperture in the cartridge, along with a spring configured to hold the locking element in the aperture. Advantageously, the cartridge may be unlocked simply by pressing a button; for example, the button may lift the rigid piece of material from the cartridge or push the locking element from the aperture.

In some embodiments, the rotors of the cartridge comprise non-circular female connectors, and shafts rotated by the motors comprise complementary male connectors on springs. Following the insertion of the cartridge, the motors are activated to rotate the shafts. Upon the male connectors aligning with the female connectors, the springs push the male connectors into the female connectors, such that the rotors begin to rotate together with the shafts.

In other embodiments, the rotors, which are typically circular, are coupled with the shafts via a pair of clutches. Each clutch comprises an outer ring, comprising an inner surface shaped to define multiple recesses, and an inner ring, which is disposed inside the outer ring and is shaped to define multiple compartments. Each compartment contains a gripping element, such as a cylindrical metallic peg, and has both a radially-inward-facing opening and a radially-outward-facing opening.

When the compartments are aligned with the recesses, the gripping elements may protrude out of the radially-outward-facing openings into the recesses, such that the gripping elements do not inhibit insertion of the rotor into the inner ring. Following the insertion of the rotor, the shafts may begin to rotate the outer ring with respect to the inner ring. This rotation causes the recesses to become misaligned with the compartments, thus forcing the gripping elements through the radially-inward-facing openings against the rotor. Thus, the gripping elements grip the rotor, such that the rotor rotates with the outer ring.

System Description

Reference is initially made to FIG. 1, which is a schematic illustration of a phacoemulsification system 20, in accordance with some embodiments of the present invention.

System 20 comprises a phacoemulsification probe 22, using which a physician 24 may perform a phacoemulsification procedure on an eye of a subject 26. In particular, physician 24 may position the distal tip of probe 22 near or against the lens of the eye. Subsequently, the physician may cause an ultrasonic transducer at the distal tip of the probe to emit ultrasonic waves at the lens, thus causing phacoemulsification of the lens.

System 20 further comprises a fluidics system 28, which is described in detail below with reference to the subsequent figures. As the phacoemulsification procedure is performed, fluidics system 28 aspirates debris (including pieces of the lens) from the eye while maintaining a flow of an irrigating fluid, such as a balanced salt solution (BSS), to the eye so as to maintain the intraocular pressure in the eye.

More specifically, fluidics system 28 comprises a cartridge 30, comprising two positive displacement pumps, and a base 50, comprising two motors. Prior to the procedure, cartridge 30 is inserted into base 50 such that each pump is mechanically coupled with a different respective motor. Subsequently, one of the pumps, driven by one of the motors, pumps fluid from a reservoir 42 to the distal end of the probe. The other pump, driven by the other motor, pumps fluid and debris from the eye to a collection container 44.

Typically, base 50 is disposed within, or is an integrated part of, a console 34, and cartridge 30 is inserted into the base through a slot 36 in a side panel 35 or top panel 37 of console 34. Following the procedure, the cartridge is removed from the base, e.g., by pushing a button 46 as further described below, for example, with reference to FIGS. 3A-B. Typically, the cartridge is then disposed of, and another cartridge is used for the next 25 procedure.

Alternatively, base 50 may be disposed within probe 22, e.g., at or near the portion of probe 22 that is grasped by physician 24.

In some embodiments, system 20 further comprises a display 48. System 20 may further comprise a processor and/or other circuitry (not shown), configured to drive the ultrasonic transducer at the tip of probe 22, control fluidics system 28, display relevant information on display 48, and/or perform any other relevant function.

The Fluidics System

A more detailed description of cartridge 30 is hereby provided with reference to FIG. 2A, which schematically shows cartridge 30 from two different perspectives, and FIG. 2B, which schematically shows a longitudinal cross section through the cartridge, in accordance with some embodiments of the present invention.

Figure 6:
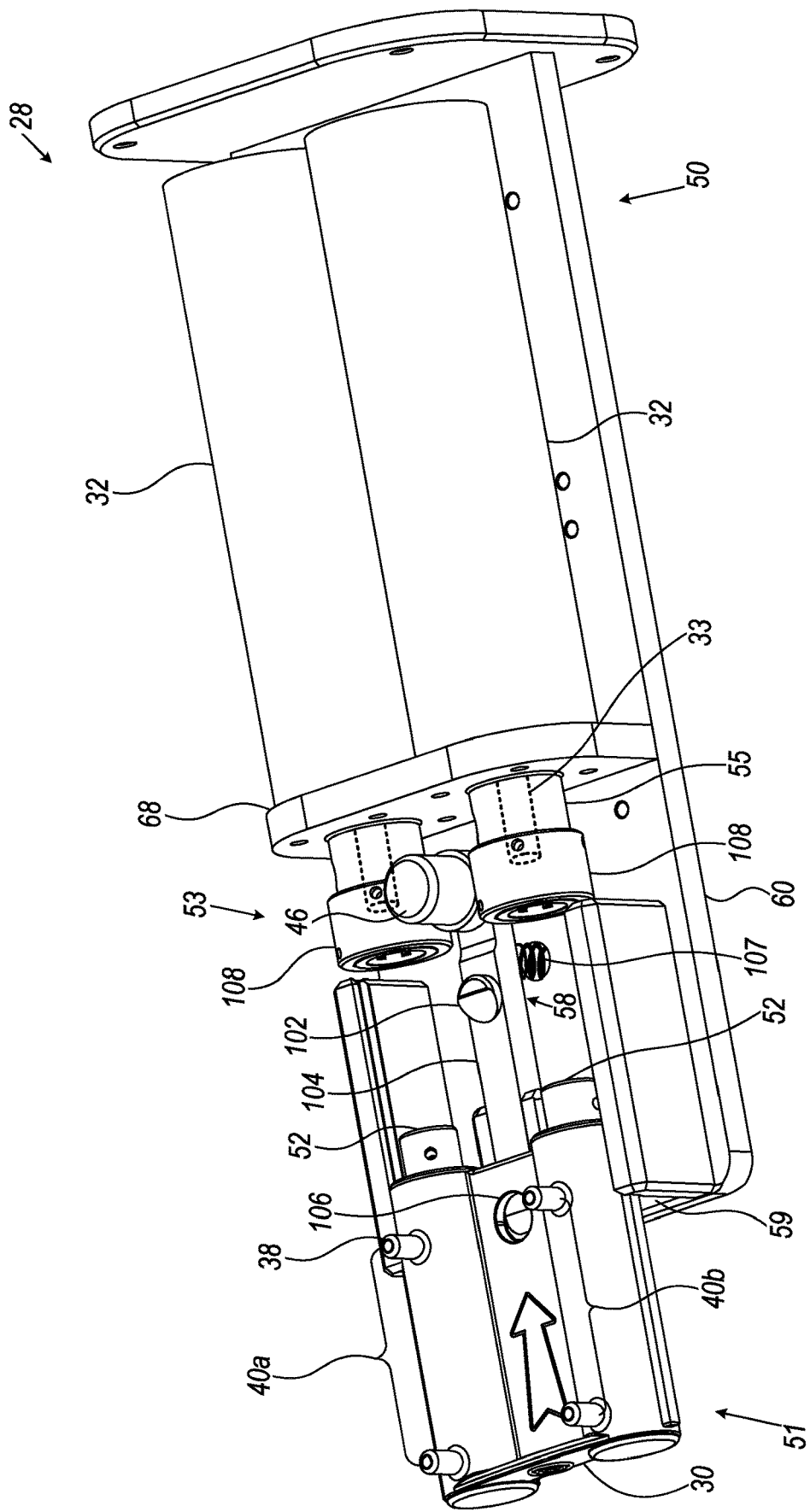
FIG. 6 is a schematic illustration of a fluidics system, in accordance with other embodiments of the present invention.

Cartridge 30 is shaped to define two stators 51 and respective pairs of ports 38 in fluidic communication with stators 51. Ports 38 may be disposed, for example, at the front of the cartridge or, as shown in FIG. 6 (described below), at another surface of the cartridge perpendicular to the front. (In these latter embodiments, the cartridge is typically inserted through a slot in top panel 37 of console 34 (FIG. 1), with holes in a side panel 35 of the console exposing the ports.) Stators 51 may be metallic or polymeric.

The cartridge further comprises two rotors 52 rotatably disposed, respectively, within the stators. (The cross section in FIG. 2B is taken through one of the stators, so as to reveal the rotor 52 disposed therein.) Rotors 52 may be metallic or polymeric.

As described above with reference to FIG. 1, typically, one pair 40a of ports 38 is connected to reservoir 42 and to the probe, while the other pair 40b of ports is connected to the probe and to collection container 44. Thus, rotation of the rotors within the stators causes (i) fluid to flow from reservoir 42, through pair 40a, to the distal tip of probe 22, and (ii) fluid and debris to flow from the eye, through pair 40b, to collection container 44.

In some embodiments, rotors 52 comprise respective connectors 54, each of which has a non-circular (e.g., hexagonal) shape and is typically female. Alternatively or additionally, the outer surface of the cartridge may be shaped to define a ridge 56. These features of the cartridge facilitate coupling the cartridge to base 50 (FIG. 1), as further described below with reference to FIGS. 4-5.

In some embodiments, cartridge 30 comprises a front panel 61, which, by virtue of being fastened to the remainder of the cartridge (e.g., via screws), stabilizes stators 51 and prevents leakage from the cartridge. Front panel 61 may be grasped when inserting the cartridge into, or removing the cartridge from, the base. Alternatively or additionally, cartridge 30 may comprise a handle, which may be grasped when inserting or removing the 10 cartridge.

Other features of the fluidics system are hereby described with reference to FIGS. 3A-B, which schematically show the fluidics system from two different perspectives, in accordance with some embodiments of the present invention.

As noted above with reference to FIG. 1, fluidics system 28 comprises a base 50, into which cartridge 30 is inserted. For example, the base may be shaped to define a slot 59, and the cartridge may be inserted into (and removed from) the base by virtue of being slid through slot 59.

In some embodiments, a front face 57 of the base is shaped to define slot 59. In such embodiments, the base may be disposed inside console 34 (FIG. 1), with front face 57 situated behind side panel 35 or top panel 37 of the console such that slot 59 is aligned with slot 36 of the console. Thus, as described above with reference to FIG. 1, the cartridge may be inserted into (and removed from) the base through slot 36.

Typically, base 50 comprises a lock 58, configured to lock the cartridge in place upon the insertion of the cartridge. Typically, the base further comprises button 46, which is configured to release lock 58 upon a pushing of the button. In some embodiments, button 46 protrudes through a hole in front face 57. This hole may be aligned with a hole in side panel 35 or top panel 37 of the console, such that, as illustrated in FIG. 1, the button protrudes from the console. An example embodiment including lock 58 and button 46 is further described below with reference to FIG. 4.

In other embodiments, the base is an integrated part of console 34, such that the base need not comprise front face 57. Rather, cartridge 30 may be inserted into the base directly through slot 36 (FIG. 1), and button 46 may protrude directly through side panel 35 or top panel 37 of the console.

Base 50 comprises two motors 32 and a mechanical coupling mechanism 53. Mechanical coupling mechanism 53 is configured to mechanically couple motors 32 to rotors 52 (FIG. 2B), such that, following the insertion of the cartridge into the base, each of the motors may be activated to rotate a different respective one of the rotors.

Typically, mechanical coupling mechanism 53 comprises two shafts 70. Each shaft 70 is mechanically coupled at its back end with a different respective motor 32. For example, shaft 70 may be directly coupled with motor 32, such that the shaft protrudes from the motor and is rotated directly by torque generated by the motor. Alternatively, as shown in FIGS. 3A-B, shaft 70 may be indirectly coupled with motor 32; for example, the shaft may be mechanically coupled to another shaft 33, which is directly coupled with the motor, via gears 72. Thus, each motor turns a different respective one of shafts 70. Each shaft 70 is also mechanically coupled at its front end with a different respective rotor. The coupling of the shaft with the rotor, along with other features of coupling mechanism 53 in some embodiments, are further described below with reference to FIG. 5.

In some embodiments, base 50 further comprises a first panel 62. In such embodiments, tracks 64 may run between front face 57 and first panel 62, and cartridge 30 may slide along tracks 64. First panel 62 may further facilitate the operation of lock 58, as further described below with reference to FIG. 4.

Alternatively or additionally, base 50 may further comprise a second panel 66, which may facilitate the operation of mechanical coupling mechanism 53 as further described below with reference to FIG. 5. Alternatively or additionally, base 50 may comprise a motor-supporting panel 68, to which the motors are fastened. Alternatively or additionally, base 50 may comprise a supporting panel 60, to which front face 57, first panel 62, second panel 66, and/or motor-supporting panel 68 are fastened.

In alternate embodiments, cartridge 30 comprises only a single rotor and stator, with base 50 comprising only a single motor. Alternatively, cartridge 30 may comprise more than two rotors and stators, with base 50 comprising more than two motors.

Locking and Releasing the Cartridge

Figure 3A:
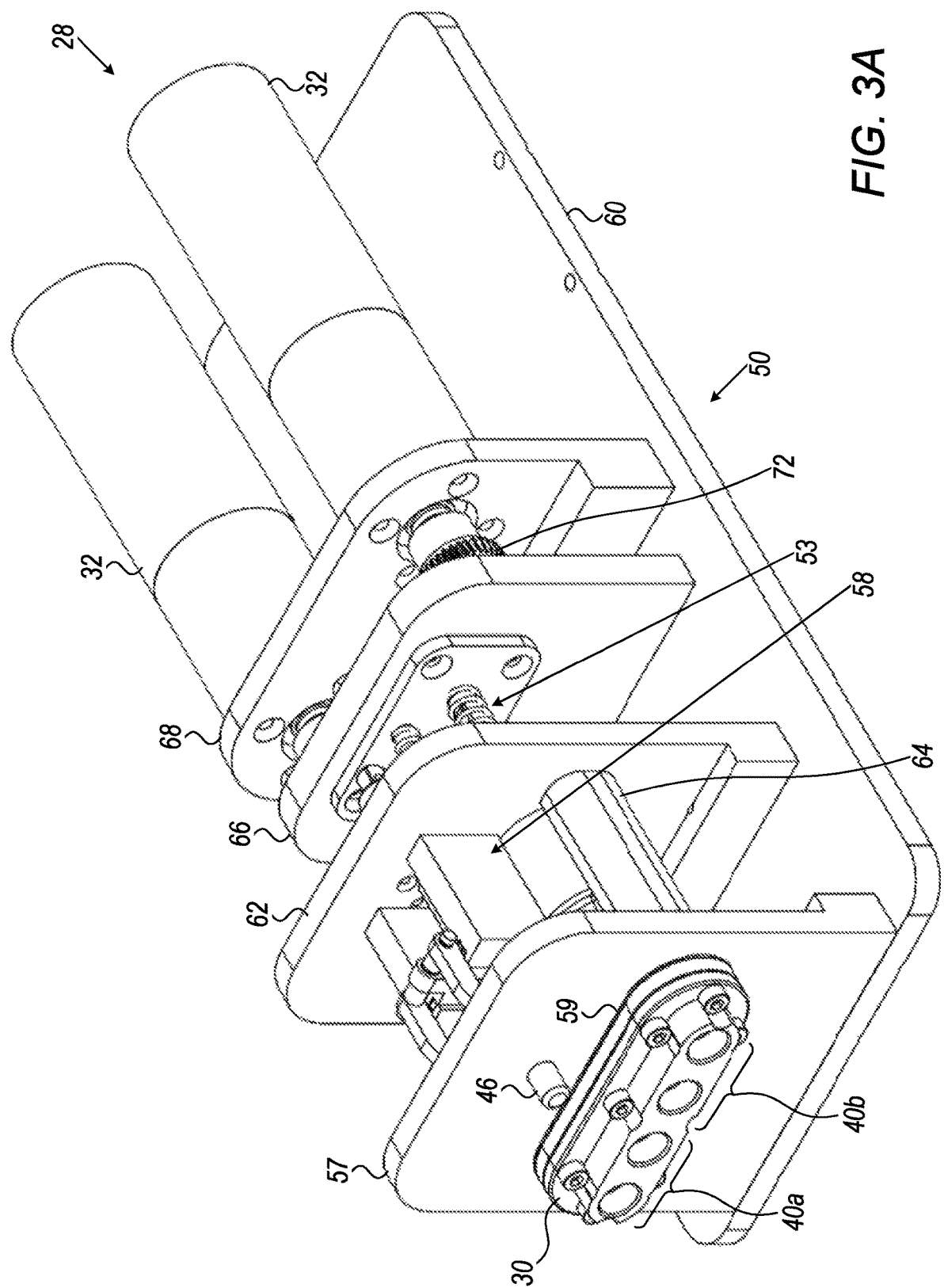
Figure 4:
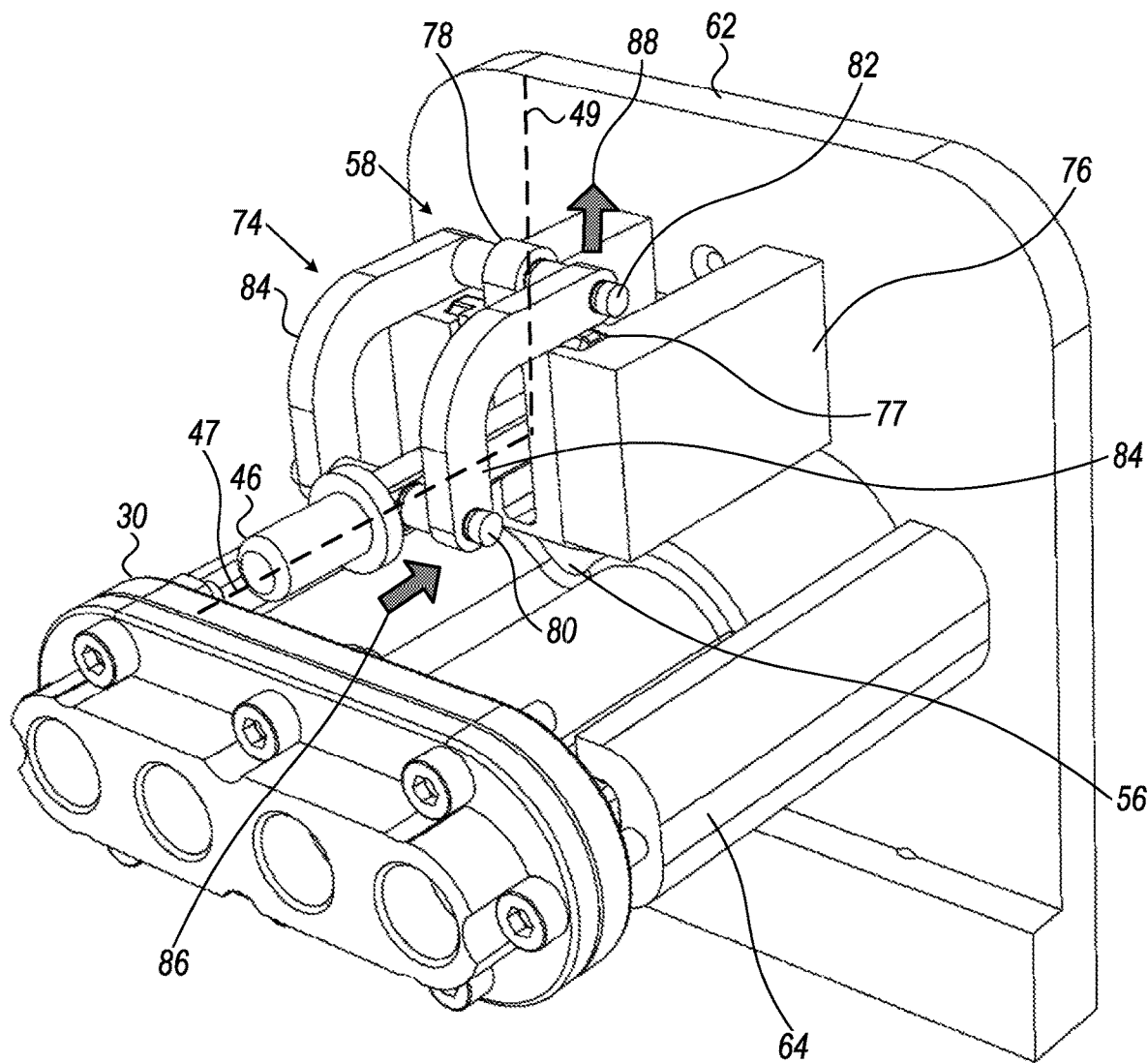
FIG. 4 schematically illustrates a locking of a cartridge in a base, in accordance with some embodiments of the present invention.

Reference is now made to FIG. 4, which schematically illustrates a locking of the cartridge in the base, in accordance with some embodiments of the present invention. (FIG. 4 shows the perspective shown in FIG. 3A, but with front face 57 and other components of the base hidden from view.)

In some embodiments, as described above with reference to FIGS. 2A-B, the outer surface of cartridge 30 is shaped to define ridge 56. In such embodiments, lock 58 may comprise a rigid piece 78 of material (e.g., metal), configured to lock the cartridge in place by resting against the ridge. For example, as shown in FIG. 4, the top surface of cartridge 30 may be shaped to define ridge 56, and rigid piece 78 may hang over the cartridge such that the bottom of rigid piece 78 rests against ridge 56. Button 46 is configured to release lock 58 by moving rigid piece 78 from ridge 56.

For example, lock 58 may further comprise a hinge 74 coupled with button 46 and with rigid piece 78, and button 46 may be configured to move rigid piece 78 by rotating hinge 74. In particular, button 46 may be configured to move along a first axis 47, and the position of rigid piece 78 along first axis 47 may be fixed. Thus, as the button is pushed along first axis 47, as indicated in FIG. 4 by a push indicator 86, the button rotates the hinge, thereby moving rigid piece 78 along a second axis 49 perpendicular to first axis 47, as indicated in FIG. 4 by a movement indicator 88. For example, for embodiments in which the cartridge and base are oriented such that rigid piece 78 hangs over the top surface of the cartridge, first axis 47 may be horizontal and second axis 49 may be vertical, i.e., a horizontal pushing of the button may lift rigid piece 78 from the cartridge. Alternatively, first axis 47 may be vertical and second axis 49 may be horizontal.

As a specific example, the base may comprise at least one anchoring element 76 coupled with first panel 62, whose position along the first axis is fixed, e.g., by virtue of being fastened to supporting panel 60 (FIGS. 3A-B). Anchoring element 76 may be shaped to define a groove 77 parallel to second axis 49, and the position of rigid piece 78 along the first axis may be fixed by virtue of rigid piece 78 being slidably disposed within groove 77. For example, as shown in FIG. 4, the rigid piece of material may be slidably disposed within grooves 77 formed within respective opposing anchoring elements 76.

Typically, hinge 74 comprises a first pin 80, which is coupled with button 46, a second pin 82, which is coupled with rigid piece 78, and two swiveling elements 84, each comprising one end rotatably coupled with first pin 80 and another end rotatably coupled with second pin 82. Button 46 moves rigid piece 78 by swiveling the swiveling elements.

Following the release of lock 58, cartridge 30 may be removed from base 50.

Referring again to FIG. 3B, in some embodiments, base 50 further comprises at least one spring 90, configured to facilitate the removal of cartridge 30. (FIG. 3B shows two such springs, one above the other.) In particular, spring 90 compresses upon the insertion of cartridge 30, remains compressed against and cartridge 30 while the cartridge is locked in place. Upon the pushing of button 46 and, consequently, the release of lock 58, spring 90 decompresses, such that the front end 94 of the spring, which is typically enlarged relative to the back end of the spring, pushes cartridge 30 from base 50.

For example, base 50 may comprise at least one rod 92 coupled with second panel 66. Spring 90 may be coiled around rod 92, with the back end of spring 90 coupled with second panel 66. Prior to the insertion of cartridge 30, spring 90 is decompressed, such that front end 94 is at its frontmost position; for example, front end 94 may pass through a hole 95 in first panel 62, with a middle portion 96 of the spring, which is larger than hole 95, resting against first panel 62. Subsequently, as the cartridge is inserted, the cartridge pushes front end 94 backward (e.g., through hole 95), thus compressing the spring. Following the release of lock 58, spring 90 springs forward, such that front end 94 pushes cartridge 30 from base 50.

The Mechanical Coupling Mechanism

Figure 5:
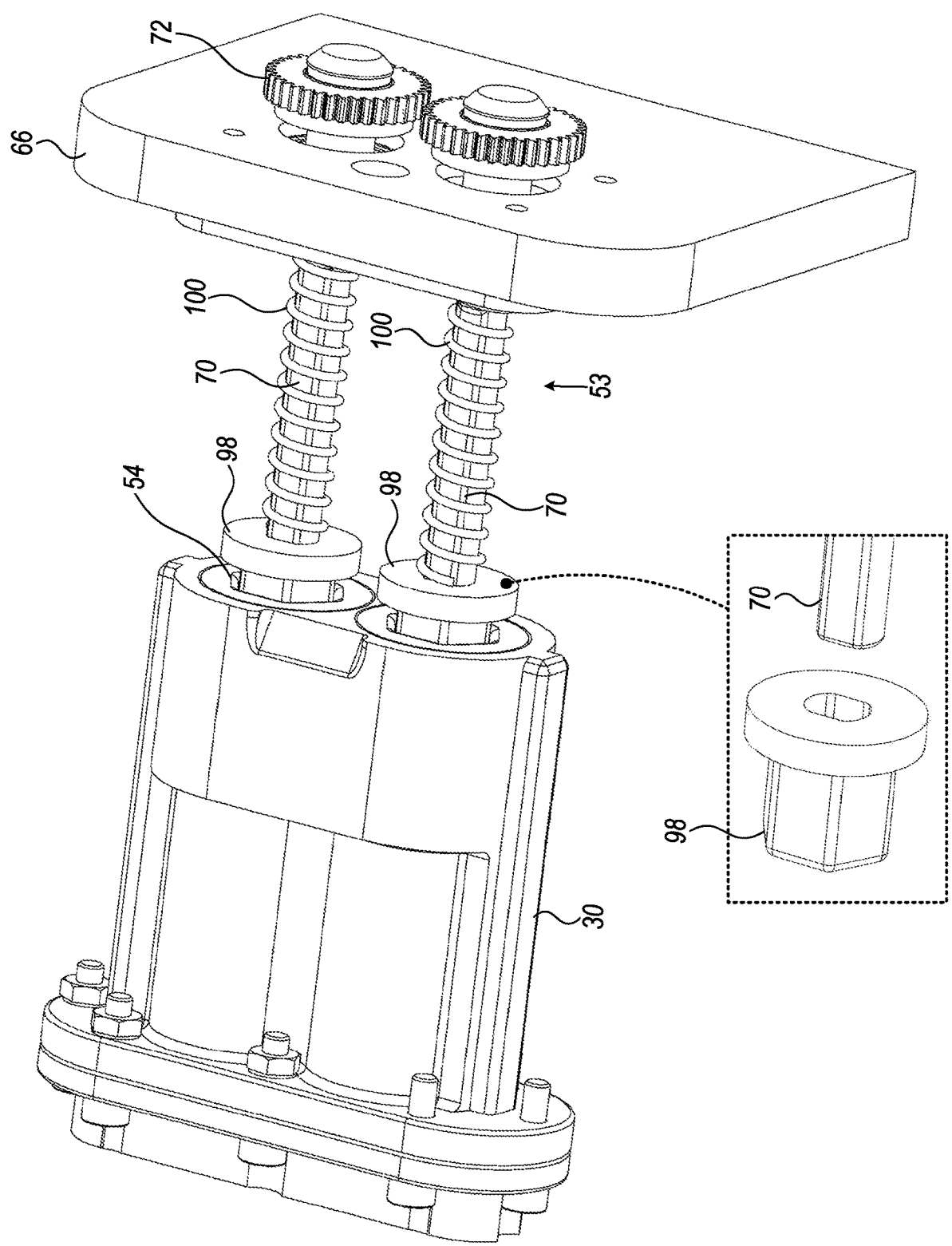
FIG. 5 is a schematic illustration of a mechanical coupling mechanism, in accordance with some embodiments of the present invention.

Reference is now made to FIG. 5, which is a schematic illustration of mechanical coupling mechanism 53, in accordance with some embodiments of the present invention. (For clarity, first panel 62 and other components of base 50 are hidden from view.)

In some embodiments, as described above with reference to FIGS. 2A-B, rotors 52 of cartridge 30 comprise respective non-circular connectors 54. In such embodiments, typically, mechanical coupling mechanism 53 comprises two complementary connectors 98 slidably disposed over shafts 70, each connector 98 having the same shape as that of connectors 54 (e.g., a hexagonal shape) and typically being male. As shown in the inset exploded view in FIG. 5, shafts 70 (along with the apertures in connectors 98 through which the shafts pass) are non-circular, such that, as motors 32 rotate shafts 70, connectors 98 rotate with shafts 70. Mechanical coupling mechanism 53 further comprises two springs 100 coiled over shafts 70, respectively. Springs 100 are configured to couple the shafts with rotors 52 by pushing s 98 toward connectors 54 such that, upon connectors 98 rotating into alignment with connectors 54, connectors 98 mate with connectors 54.

For example, the back ends of springs 100 may be coupled with second panel 66, and the front ends of springs 100 may be coupled with connectors 98. If, upon insertion of cartridge 30, connectors 98 are misaligned with connectors 54, cartridge 30 may push connectors 98 backward, thus compressing springs 100. Upon connectors 98 rotating into alignment with connectors 54, springs 100 decompress and push connectors 98 forward, thus causing connectors 98 to mate with connectors 54.

Following the mating of connectors 98 with connectors 54, the rotors in cartridge 30 may be rotated by motors 32 (FIGS. 3A-B).

Alternate Lock

Reference is now made to FIG. 6, which is a schematic illustration of fluidics system 28 in accordance with other embodiments of the present invention.

In the example shown in FIG. 6, cartridge 30 is shaped to define an aperture 106, which may pass fully or partially through cartridge 30. (Typically, aperture 106 is positioned between stators 51.) Lock 58 comprises a locking element 102, which is shaped to fit into aperture 106. For example, lock 58 may comprise an arm 104, from which locking element 102 protrudes. Typically, lock 58 further comprises a spring 107, configured to lock cartridge 30 in place by holding locking element 102 in aperture 106.

For example, cartridge 30 may be pushed into base 50 over arm 104. As cartridge 30 slides over locking element 102, cartridge 30 may push locking element 102 down, thus compressing spring 107. Upon aperture 106 becoming aligned with locking element 102, spring 107 may decompress, thus pushing locking element 102 into aperture 106 and locking cartridge 30 in place.

Button 46 is configured to release lock 58 by pushing locking element 102 from aperture 106. For example, button 46 may push arm 104 away from cartridge 30, such that locking element 102 exits aperture 106. While button 46 is depressed, cartridge 30 may be pulled from base 50. Alternatively, as described above with reference to FIG. 3B, base 50 may comprise another spring analogous to spring 90, configured to push cartridge 30 from base 50 upon the release of lock 58.

Alternate Mechanical Coupling Mechanism

Alternatively or additionally to the alternate lock shown in FIG. 6, fluidics system 28 may comprise an alternate embodiment of mechanical coupling mechanism 53 comprising two clutches 55, as shown in FIG. 6. Each clutch 55 is configured to mechanically couple a rotor 52 with a motor 32. An advantage of this alternate embodiment is that rotors 52 need not necessarily comprise non-circular connectors 54 (FIG. 5).

For example, clutches 55 may be positioned in front of motor-supporting panel 68. Shafts 33 may pass through motor-supporting panel 68 and into clutches 55 from the rear, while rotors 52 may be inserted into clutches 55 from the front. Alternatively, shafts 33 may be mechanically coupled to other shafts (e.g., via gears 72 as in FIGS. 3A-B), and these latter shafts may enter clutches 55 from the rear.

Figure 7A:
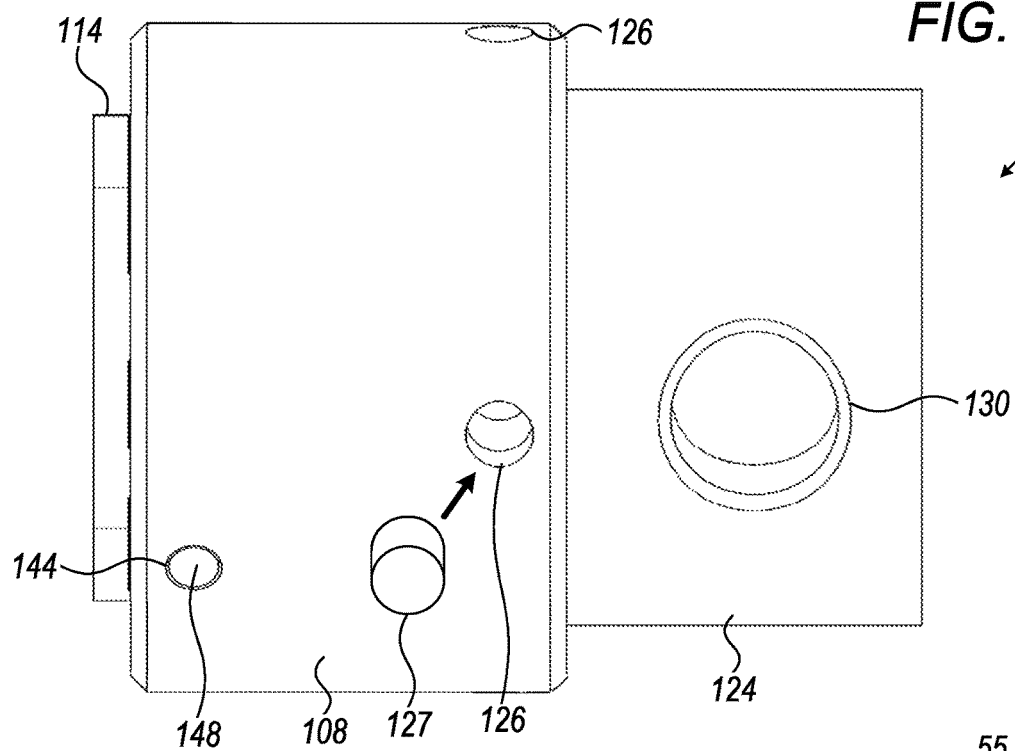
FIGS. 7A-B schematically show a clutch from two different perspectives, in accordance with some embodiments of the present invention.
Figure 7B:
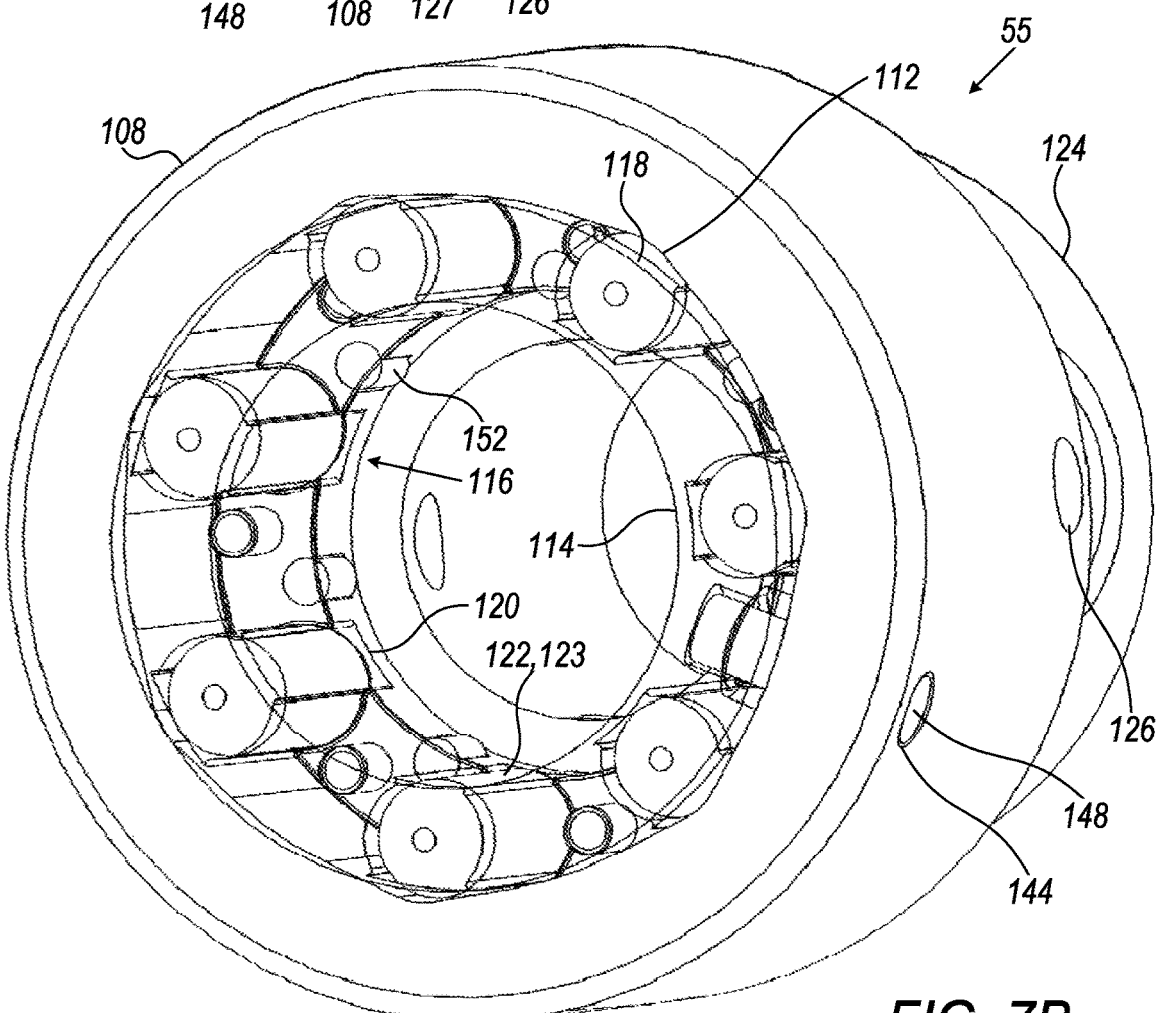
Figure 8:
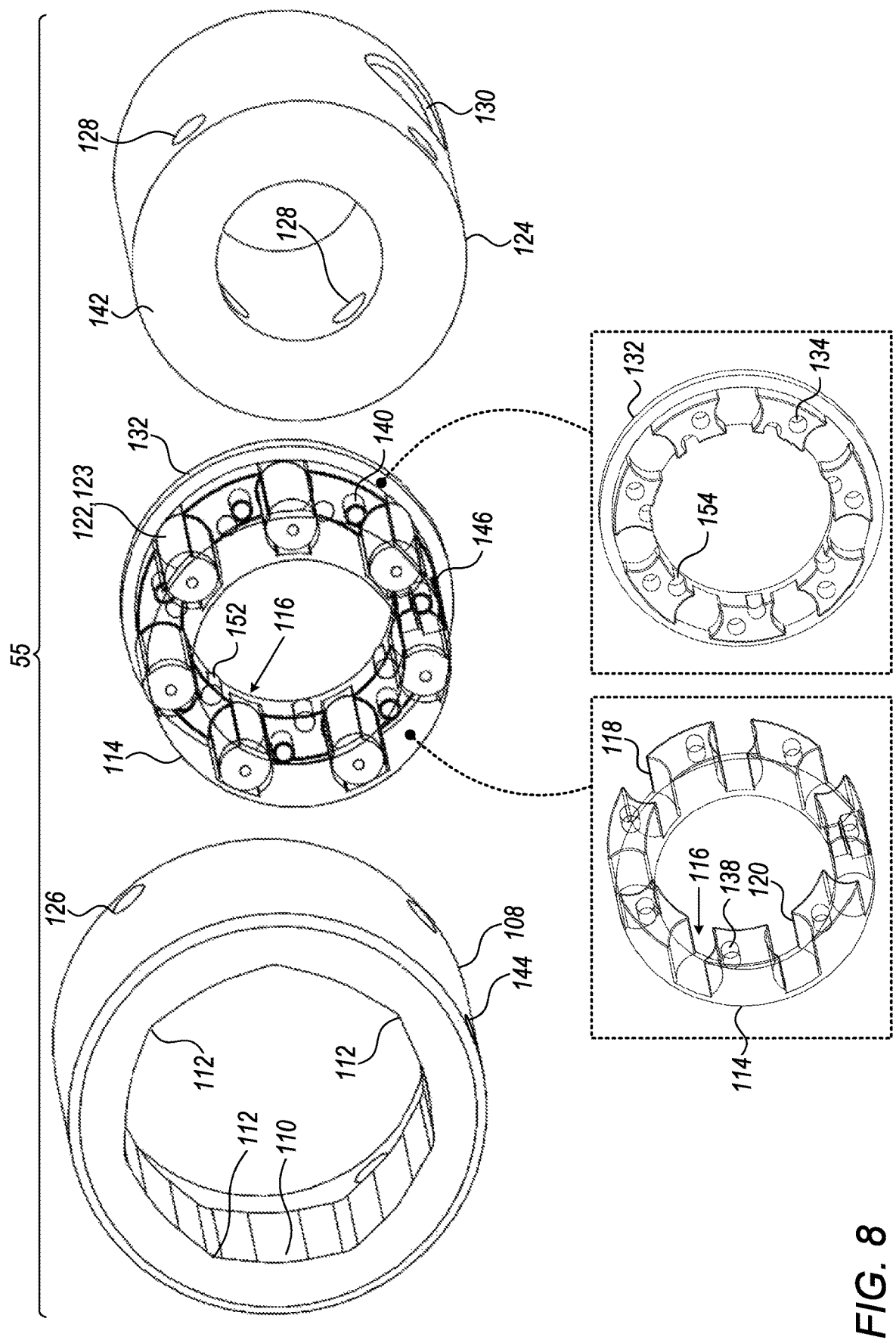
FIG. 8 schematically shows an exploded view of a clutch, in accordance with some embodiments of the present invention.

For further details, reference is additionally made to FIGS. 7A-B, which schematically show a clutch 55 from two different perspectives, and to FIG. 8, which schematically shows an exploded view of the clutch, in accordance with some embodiments of the present invention.

Clutch 55 comprises an outer ring 108 comprising an inner surface 110 shaped to define multiple recesses 112. Clutch 55 further comprises an inner ring 114 disposed within outer ring 108. Inner ring 114 is shaped to define multiple compartments 116 having respective outer openings 118, which face outer ring 108 (in particular, inner surface 110 of outer ring 108), and respective inner openings 120 opposite outer openings 118. Typically, the number of compartments 116 is the same as the number of recesses 112. For example, FIGS. 7A-B and 8 show an embodiment having seven compartments 116 and seven recesses 112.

In some embodiments, clutch 55 further comprises an inner-ring support 132, which is positioned behind inner ring 114, i.e., between inner ring 114 and motors 32. In some such embodiments, support 132 is coupled with inner ring 114. For example, inner-ring support 132 may be shaped to define multiple apertures 134, and inner ring 114 may be shaped to define corresponding apertures 138 situated between compartments 116. Inner ring 114 may be placed onto inner-ring support 132 such that apertures 138 are aligned with apertures 134, and pegs 140 may then be passed through the apertures so as to hold inner ring 114 to inner-ring support 132.

Clutch 55 further comprises multiple gripping elements 122 disposed within compartments 116, respectively. Gripping elements 122 may be made from a metal or any other rigid material.

Typically, the portion of each gripping element 122 that faces inner surface 110 is curved. For example, gripping elements 122 may comprise respective cylindrical pegs 123, which are disposed within compartments 116 such that the round surfaces of pegs 123 face inner surface 110. Alternatively, gripping elements 122 may comprise respective balls.

Outer ring 108 is configured to couple with a shaft coupled with a motor 32, such as shaft 33 (FIG. 6), such that motor 32 rotates outer ring 108 by rotating the shaft. For example, outer ring 108 may be coupled with a connecting ring 124 behind inner ring 114, and connecting ring 124 may be fastened to shaft 33, such that outer ring 108 is coupled with shaft 33 by virtue of connecting ring 124 being fastened to the shaft.

For example, to assemble clutch 55, following the coupling of inner ring 114 to inner-ring support 132, inner-ring support 132 may be placed against the front-facing surface 142 of connecting ring 124. Subsequently, outer ring 108 may be placed over inner ring 114 and inner-ring support 132, such that the backmost portion of outer ring 108 overlaps the frontmost portion of connecting ring 124. Subsequently, outer ring 108 may be coupled with connecting ring 124 using any suitable technique. For example, outer ring 108 may be shaped to define multiple apertures 126, and connecting ring 124 may be shaped to define corresponding apertures 128. Following the placement of outer ring 108 over connecting ring 124 such that apertures 126 are aligned with apertures 128, pegs 127 may be inserted through apertures 126 and apertures 128, as shown in FIG. 7A.

Alternatively, for example, inner ring 114 may be inserted into outer ring 108, e.g., such that inner-ring support 132 rests against the back-facing surface of outer ring 108. Subsequently, connecting ring 124 may be placed over outer ring 108 and then coupled with outer ring 108, e.g., using pegs 127 as described above.

To fasten connecting ring 124 to shaft 33 (or to another shaft mechanically coupled thereto), the shaft may be inserted into connecting ring 124 (or connecting ring 124 may be inserted into the shaft), and the shaft may then be screwed to the connecting ring via a screw-hole 130 in connecting ring 124. Alternatively, any other suitable technique may be used.

Alternatively, the shaft may be coupled directly to outer ring 108. For example, the shaft may be screwed to outer ring 108 via a screw-hole in the outer ring.

Inner ring 114 is configured to receive rotor 52 (FIG. 6), which protrudes backward from the body of cartridge 30, while compartments 116 are aligned with recesses 112, by virtue of gripping elements 122 sitting at least partially within recesses 112. In other words, when compartments 116 are aligned with recesses 112, gripping elements 122 may sit at least partially within recesses 112, such that gripping elements 122 do not inhibit the insertion of rotor 52.

Following the insertion of cartridge 30 into base 50 (and hence the insertion of rotors 52 of cartridge 30 into the respective inner rings 114 of clutches 55), the motors may be activated to rotate motor shafts 33, and hence, outer rings 108. This rotation causes compartments 116 to become misaligned with recesses 112, thereby causing outer ring 108 to push gripping elements 122, through outer openings 118, against rotor 52, through inner openings 120. In other words, outer ring 108 pushes gripping elements 122 radially inward, against rotor 52. Thus, gripping elements 122 grip rotor 52, such that, shortly after outer ring 108 begins to rotate, inner ring 114 and rotor 52 begin to rotate with outer ring 108.

In some embodiments, outer ring 108 is shaped to define a radial aperture 144, and inner ring 114 is shaped to define another, inner radial aperture 146 aligned with outer radial aperture 144. In such embodiments, clutch 55 further comprises a compressible peg 148, such as a rubber peg, passing through outer radial aperture 144 and inner radial aperture 146.

Figure 9:
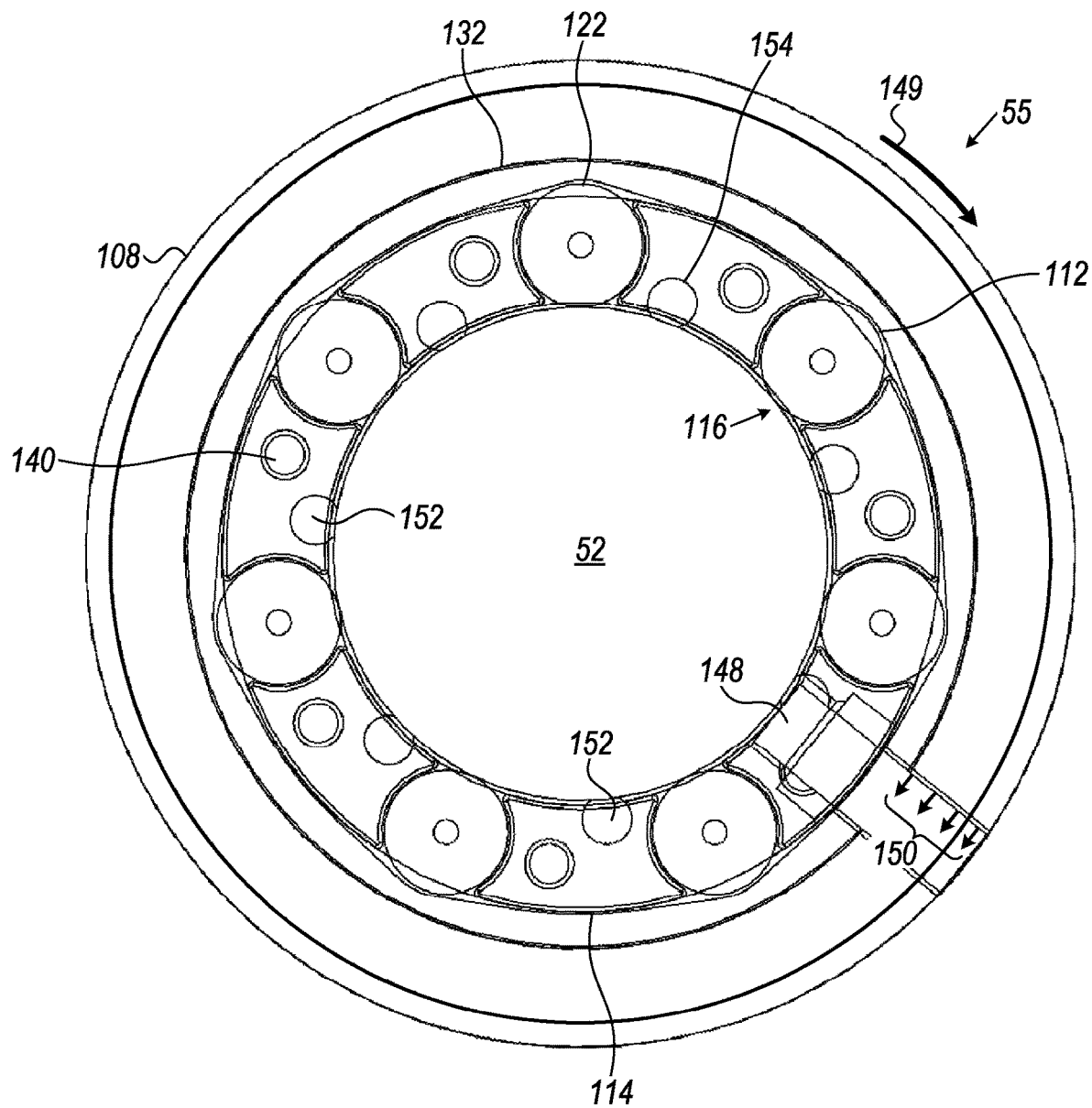
FIG. 9 is a schematic illustration of a clutch clutching a rotor, in accordance with some embodiments of the present invention.

The function of compressible peg 148 is hereby described with reference to FIG. 9, which is a schematic illustration of clutch 55 clutching a rotor 52, in accordance with some embodiments of the present invention. FIG. 9 shows a view from the front of clutch 55, with cartridge 30—aside from the protruding back portion of rotor 52—hidden from view, and with outer ring 108 rendered transparent.

During the rotation of shaft 33 together with outer ring 108, compressible peg 148 becomes and remains compressed. In particular, as the outer ring begins to rotate, as indicated in FIG. 9 by a rotation indicator 149, compressible peg 148 becomes compressed, as indicated in FIG. 9 by a compression indicator 150. Subsequently, as outer ring 108 continues to rotate (together with inner ring 114, as described above), compressible peg 148 remains compressed.

Upon shaft 33 and outer ring 108 ceasing to rotate, compressible peg 148 decompresses, thereby realigning compartments 116 with recesses 112. Due to this realignment, gripping elements 122 release their grip on rotor 52, such that cartridge 30 may be easily removed from base 50, e.g., following the unlocking of cartridge 30 as described above with reference to FIG. 4 or FIG. 6. Another rotor 52 may then be inserted into inner ring 114 during insertion of the next cartridge 30.

In some embodiments, clutch 55 further comprises multiple compressible elements 152, such as rubber pegs, arranged around the inner circumference of inner ring 114. For example, compressible elements 152 may be disposed within additional compartments 154 in inner ring 114. Compressible elements 152 are configured to compress upon insertion of rotor 52 into inner ring 114, thereby centering rotor 52 within inner ring 114.

As noted above, the alternate mechanical coupling mechanism of FIGS. 6-9 is not contingent on the alternate lock of FIG. 6, and the alternate lock is not contingent on the alternate mechanical coupling mechanism. Thus, for example, the alternate mechanical coupling mechanism of FIGS. 6-9 may be combined with the lock of FIG. 4, and the mechanical coupling mechanism of FIGS. 3A-B may be combined with the alternate lock of FIG. 6.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. An apparatus for mechanically coupling a motor to a rotor, the apparatus comprising:

an outer ring comprising an inner surface shaped to define multiple recesses, wherein the outer ring is shaped to define an outer radial aperture;

an inner ring disposed within the outer ring and shaped to define multiple compartments having respective outer openings, which face the outer ring, and respective inner openings opposite the outer openings, wherein the inner ring is shaped to define an inner radial aperture aligned with the outer radial aperture;

multiple gripping elements disposed within the compartments, respectively, the inner ring being configured to receive the rotor while the compartments are aligned with the recesses, by virtue of the gripping elements sitting at least partially within the recesses, and the outer ring being configured to couple with a shaft coupled with the motor such that rotation of the shaft by the motor causes the compartments to become misaligned with the recesses, thereby causing the outer ring to push the gripping elements, through the outer openings, against the rotor, through the inner openings; and a compressible peg passing through the outer radial aperture and the inner radial aperture, the compressible peg being configured to:

become and remain compressed during the rotation of the outer ring, and decompress following the rotation of the shaft, thereby realigning the compartments with the recesses.

2. The apparatus according to claim 1, wherein the gripping elements comprise respective cylindrical pegs.

3. The apparatus according to claim 1, wherein the gripping elements comprise respective balls.

4. The apparatus according to claim 1, further comprising a connecting ring coupled with the outer ring behind the inner ring, wherein the outer ring is configured to couple with the shaft by virtue of the connecting ring being fastened to the shaft.

5. An apparatus for mechanically coupling a motor to a rotor, the apparatus comprising:

an outer ring comprising an inner surface shaped to define multiple recesses;

an inner ring disposed within the outer ring and shaped to define multiple compartments having respective outer openings, which face the outer ring, and respective inner openings opposite the outer openings;

multiple gripping elements disposed within the compartments, respectively, the inner ring being configured to receive the rotor while the compartments are aligned with the recesses, by virtue of the gripping elements sitting at least partially within the recesses, and the outer ring being configured to couple with a shaft coupled with the motor such that rotation of the shaft by the motor causes the compartments to become misaligned with the recesses, thereby causing the outer ring to push the gripping elements, through the outer openings, against the rotor, through the inner openings; and multiple compressible elements arranged around an inner circumference of the inner ring, the compressible elements being configured to compress upon insertion of the rotor into the inner ring, thereby centering the rotor within the inner ring.

* * * * *